United States Patent
Wang et al.

(10) Patent No.: US 10,639,314 B1
(45) Date of Patent: *May 5, 2020

(54) METHOD OF TREATING ALZHEIMER'S DISEASE

(71) Applicant: LA PharmaTech Inc., Blacksburg, VA (US)

(72) Inventors: Jianmin Wang, Blacksburg, VA (US); Geping Cui, Beijing (CN)

(73) Assignee: LA PharmaTech Inc., Blacksburg, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/398,845

(22) Filed: Apr. 30, 2019

(51) Int. Cl.
    *A61K 31/55*    (2006.01)
    *A61P 25/28*    (2006.01)
    *A61K 9/00*     (2006.01)

(52) U.S. Cl.
    CPC .......... *A61K 31/55* (2013.01); *A61K 9/0053* (2013.01); *A61P 25/28* (2018.01)

(58) Field of Classification Search
    CPC .............................. A61K 31/55; A61P 25/28
    See application file for complete search history.

(56) References Cited

U.S. PATENT DOCUMENTS

| | | | |
|---|---|---|---|
| 6,849,621 B2 | 2/2005 | Rosenblum et al. |
| 7,220,735 B2 | 5/2007 | Ting et al. |
| 7,355,042 B2 | 4/2008 | Edgar et al. |
| 7,615,550 B2 | 11/2009 | Heightman et al. |
| 7,786,161 B2 | 8/2010 | Tani et al. |
| 9,278,092 B2 | 3/2016 | Chase et al. |
| 2009/0318703 A1 | 12/2009 | Tani et al. |
| 2010/0152108 A1 | 6/2010 | Hung et al. |
| 2018/0116979 A1 | 5/2018 | Clarence-Smith et al. |

FOREIGN PATENT DOCUMENTS

| | | |
|---|---|---|
| WO | 2006058022 A1 | 6/2006 |
| WO | 2014018563 A3 | 5/2014 |

OTHER PUBLICATIONS

Hatakeyama et al. Geriatr. Gerontol. Int., 2008, vol. 8, pp. 59-61 (Year: 2008).*
Riethmuller et al. Arzneimittel-Forschung, 1994, vol. 44, No. 10, pp. 1136-1140 (Abstract attached) (Year: 1994).*
Aricept, Generic Name: donepezil hydrochloride, Brand Name: Aricept, Drug Description, RxList.com, Jan. 3, 2019.
Bezprozvanny, Ilya. The rise and fall of Dimebon. National Institute of Health. Feb. 12, 2014.
Category H1 receptor antagonists. Wikipedia. Sep. 20, 2012.
Co-Pending U.S. Appl. No. 16/382,885, Response to restriction requirement dated Oct. 2, 2019, 3 pgs.
Co-Pending U.S. Appl. No. 16/382,885, Restriction Requirement dated Aug. 9, 2019, 7 pgs.
Co-Pending U.S. Appl. No. 16/418,614, Non-Final Office Action dated Aug. 6, 2019, 31 pages.
Co-Pending U.S. Appl. No. 16/418,614, Response to Non-Final Office Action dated Nov. 6, 2019, 10 pages.
Co-pending U.S. Appl. No. 16/424,788 Response to Restriction Requirement, dated Oct. 2, 2019, 3 pgs.
Co-pending U.S. Appl. No. 16/424,788 Restriction Requirement, dated Aug. 9, 2019, 7 pgs.
Co-Pending U.S. Appl. No. 16/426,121, Non-Final Office Action dated Aug. 6, 2019, 25 pages.
Co-Pending U.S. Appl. No. 16/426,121, Response to Non-Final Office Action dated Nov. 6, 2019, 9 pages.
Co-pending application No. PCT/US19/29885 International Search Report dated Jul. 15, 2019. 7 pages.
Co-pending application No. PCT/US19/33359 International Search Report and Written Opinion dated Aug. 15, 2019. 9 pages.
Co-Pending Application No. PCT/US2019/027293, Search Report & Written Opinion, dated Sep. 17, 2019, 8 pages.
Hansen et al. Clinical Interventions in Aging 2008, vol. 3, No. 2, pp. 211-225.
Naddafi, F., Mirshafiey A., The neglected role of histamine in Alzheimer's disease., Jun. 2013;28(4):327-36. doi: 10.1177/1533317513488925. Epub May 15, 2013.
Sedeyn, Jonathan Histamine Induces Alzheimer's Disease-Like Blood Brain Barrier Breach and local cellular Responses in Mouse Brain Organotypic Culture. Hindawi. Aug. 21, 2015.
St-Jean, Genevieve; Turcotte, Isabelle; Bastien, Celyne H. Cerebral asymmetry in insomnia sufferers. Frontiers in Neurology 2012, 3, 1-12.

* cited by examiner

*Primary Examiner* — James D. Anderson
(74) *Attorney, Agent, or Firm* — New River Valley IP Law, P.C.; Michele L. Mayberry

(57) ABSTRACT

Methods of treating patients suffering from or exhibiting symptoms of mental, behavioral, and/or cognitive disorders with azelastine or a pharmaceutically acceptable salt of azelastine is disclosed.

9 Claims, No Drawings

METHOD OF TREATING ALZHEIMER'S DISEASE

FIELD OF THE INVENTION

The invention relates to the field of practical medicine, namely, to the use of pharmaceutical compositions exhibiting a neurotropic action, alleviating manifestations of mental, behavioral, or cognitive disorders in cases of organic damage of various origin to the central nervous system.

BACKGROUND OF THE INVENTION

Alzheimer's disease (AD) is a progressive, chronic neurodegenerative disease that usually starts slowly and gradually worsens over time. AD is the most common cause of dementia among older adults. Dementia is the loss of cognitive functioning—thinking, remembering, and reasoning—and behavioral abilities to such an extent that it interferes with a person's daily life and activities. In its early stages, memory loss is mild, but with late-stage AD, individuals lose the ability to carry on a conversation and respond to their environment. If untreated, AD ultimately leads to death. Although the speed of progression can vary, the typical life expectancy following diagnosis is three to nine years.

A central mechanism in learning and memory is long-term potentiation (LTP). LTP is mediated by the neurotransmitter glutamate via the N-Methyl-D-aspartic acid (NMDA) receptor. The NMDA receptors can be found diffusely throughout the brain. However, they densely populate the dendrites of pyramidal cells in the hippocampus and cortex (areas known to be involved in cognition, learning, and memory). In addition to the relationship between LTP and learning, elevated glutamate levels are associated with excitotoxicity. Chronic low-dose administration of NMDA receptor agonists has been shown to induce apoptosis, while high doses induce necrosis. The activation of glutamate receptors has also been found to induce the release of glutamate. Thus, a large build-up of glutamate can occur and induce a massive accumulation of Ca2+, leading to apoptosis. It was also noted that amyloid-beta (AB) plaques increase a neuron's vulnerability to excitotoxicity. AB plaques, a pathological feature of AD, were found to induce depolarization of astrocytes, extracellular accumulation of glutamate, and intracellular deposition of Ca2+. Therefore, the glutamate-induced excitotoxicity pathway made an excellent target for the therapy of AD.

Under physiologic conditions, the glutamate released by neurons is metabolized or taken up by neighboring cells. When these pathways are disrupted, the accumulated glutamate overexcites the NMDA receptor and induces pathology characteristic of neurodegenerative diseases. NMDA receptors act as a calcium [II] ion (Ca2+) channel that activates when bound by glycine, glutamate, and/or NMDA. However, the channel functions only when the cell membrane is depolarized due to the blockade of the channel by the magnesium [II] ion (Mg2+). This prevents the influx of Ca2+ when the neuron is at rest. Under pathological conditions, such as a chronically depolarized membrane, Mg2+ leaves the channel and neuronal metabolism is inhibited, leading to cell death. When this happens, the Ca2+ influx is unrestricted for a longer period of time than normal. This influx of Ca2+ contributes to an alteration of cell function, leading to cell death either through free radicals or through overload of the mitochondria, resulting in free radical formation, caspase activation, and the release of apoptosis-inducing factors. Antagonists to the NMDA vary in affinity and in site of action, resulting in different alterations to the channel. Regardless of the mechanism of action, antagonists decrease the permeability of the channel and prevent an influx of Ca2+. Thus NMDA receptor antagonists are looked to as possible neuroprotective agents and potential therapies for neurodegenerative disease.

Most NMDA antagonists are competitive antagonists and are not well tolerated by patients due to side effects, which can include hallucinations and schizophrenia-type symptoms. The side effects likely result from the competitive antagonists blocking physiological functions of the NMDA receptor. Its role in cognition, memory, and learning make it necessary that any drug using the NMDA receptor as a target of action must preserve physiologic function to be therapeutically useful. Memantine acts on activated NMDA receptors by binding to a site located in the channel of the receptor. However, memantine will not cure AD or prevent the loss of these abilities at some time in the future. So AD has no current cure, and our effort is to find better ways to reverse the disease, delay and prevent it from developing.

On the other hand, the genetic, cellular, and molecular changes associated with AD support the evidence that activated immune and inflammatory processes is a part of the disease. Also a strong benefit of long-term use of NSAIDs was shown in epidemiological studies. So it is generally accepted that AD is partially an inflammatory disease and that inhibiting inflammation is an option of treating AD.

Inflammation clearly occurs in pathologically vulnerable regions of the AD brain, and it does so with the full complexity of local peripheral inflammatory responses. In the periphery, degenerating tissue and the deposition of highly insoluble abnormal materials are classical stimulants of inflammation. Likewise, in the AD brain damaged neurons and neurites and highly insoluble amyloid β peptide deposits and neurofibrillary tangles provide obvious stimuli for inflammation. Because these stimuli are discrete, micro-localized, and present from early preclinical to terminal stages of AD, local upregulation of complement, cytokines, acute phase reactants, and other inflammatory mediators is also discrete, micro-localized, and chronic. Cumulated over many years, direct and bystander damage from AD inflammatory mechanisms is likely to significantly exacerbate the very pathogenic processes that gave rise to it. Thus, animal models and clinical studies so far strongly suggest that AD inflammation significantly contributes to AD pathogenesis. By better understanding AD inflammatory and immune-regulatory processes, it should be possible to develop anti-inflammatory approaches that may reverse or delay or prevent developing of this devastating disorder.

Azelastine is classified pharmacologically as a second generation antihistamine and is a relatively selective, non-sedating, competitive antagonist at H1 receptors. More uniquely, its inhibition of inflammatory mediators, in addition to antihistaminic and mast cell stabilizing effects, places it among the new generation of dual-acting anti-inflammatory drugs. In addition to azelastine's high affinity for H1 receptors, its ability to modify several other mediators of inflammation and allergy contributes to its mechanism of action. In vitro and in vivo studies, as well as clinical trials support the dual effects of direct inhibition and stabilization of inflammatory cells. In vitro data indicate that azelastine's affinity for H1 receptors is estimated to be several times greater than that of chlorpheniramine, a first-generation H1 antagonist. Azelastine has only weak affinity for H2 receptors. Release of histamine from mast cells is also inhibited possibly by reversible inhibition of voltage-dependent L-type calcium channels. Inhibition of mast cell degranulation may also decrease the release of other inflammatory mediators, including leukotrienes and interleukin-1β, among others. Azelastine also directly antagonizes other mediators of inflammation, such as tumor necrosis factor-α, leukotrienes, endothelin-1, and platelet-activating factor.

SUMMARY OF THE INVENTION

The present invention includes the discovery of a method of administering azelastine or a pharmaceutically acceptable salt of azelastine to patients for treating mental, behavioral, cognitive disorders.

In some embodiments of this invention, the pharmaceutically acceptable salt of azelastine is azelastine hydrochloride.

In some embodiments of this invention, azelastine hydrochloride is provided in a daily effective amount of about 4 mg to about 40 mg.

The present invention also includes an oral pharmaceutical dosage form of the pharmaceutically acceptable salt form of azelastine that is a solid form or a liquid form.

The present invention further includes the medical use of the oral pharmaceutical dosage form of azelastine or a pharmaceutically acceptable salt of azelastine which includes administering the dosage form to patients with mental, behavioral, cognitive disorders, such as Alzheimer's disease, vascular dementia, Huntington's disease, frontal temporal dementia, traumatic brain injury, corticobasal degeneration, and/or Parkinson's disease.

In some embodiments of this invention, an oral pharmaceutical dosage form of azelastine hydrochloride in a daily effective amount of about 8 mg to about 16 mg is administered to patients with Alzheimer's disease once daily or twice daily.

DETAILED DESCRIPTION OF THE INVENTION

The inventors of the present invention surprisingly found that higher oral dosages of azelastine or a pharmaceutically acceptable salt of azelastine are suitable for treating patients suffering from mental, behavioral, cognitive disorders.

The detailed description provided below is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

Definitions

As used in the present specification, the following words and phrases are generally intended to have the meanings as set forth below, except to the extent that the context in which they are used indicates otherwise.

Mental, behavioral, cognitive disorders include Alzheimer's disease, vascular dementia, Huntington's disease, frontal temporal dementia, traumatic brain injury, corticobasal degeneration, or Parkinson's disease, and combinations of any thereof and other neurodegenerative disorders.

As used herein, the term "azelastine" refers to azelastine free base, or 4-(p-Chlorobenzyl)-2-(hexahydro-1-methyl-1H-azepin-4-yl)-1-(2H)-phthalazinone. In certain embodiments, azelastine also includes any pharmaceutically acceptable salt, such as the hydrochloride or HCl salt. Preferably, in any embodiments of the invention as described herein, azelastine is in the form of its hydrochloride salt, as azelastine hydrochloride or azelastine HCl. More preferably, in any embodiment of the invention as described herein, reference to the amounts and dosage ranges of azelastine in the oral dosage forms are to the amounts and dosage ranges of azelastine hydrochloride.

As used herein, the term "pharmaceutically acceptable salt" refers to a salt of azelastine formed with an acid selected from a group of acids consisting of 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid (L), aspartic acid (L), benzenesulfonic acid, benzoic acid, camphoric acid (+), camphor-10-sulfonic acid (+), capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, glucoheptonic acid (D), gluconic acid (D), glucuronic acid (D), glutamic acid, glutaric acid, glycerophosphoric acid, glycolic acid, hippuric acid, hydrobromic acid, hydrochloric acid, isobutyric acid, lactic acid (DL), lactobionic acid, lauric acid, maleic acid, malic acid (−L), malonic acid, mandelic acid (DL), methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, pyroglutamic acid (−L), salicylic acid, sebacic acid, stearic acid, succinic acid, sulfuric acid, tartaric acid (+L), thiocyanic acid, toluenesulfonic acid (p), undecylenic acid.

As used herein, "treating" or "treatment" means complete cure or incomplete cure, or it means that the symptoms of the underlying disease or associated conditions are at least reduced and/or delayed, and/or that one or more of the underlying cellular, physiological, or biochemical causes or mechanisms causing the symptoms are reduced, delayed and/or eliminated. It is understood that reduced or delayed, as used in this context, means relative to the state of the untreated disease, including the molecular state of the untreated disease, not just the physiological state of the untreated disease.

The term "effective amount" refers to an amount that is therapeutically sufficient to effect treatment, as defined below, when administered to a mammal in need of such treatment. The therapeutically effective amount will vary depending upon the patient being treated, the weight and age of the patient, the severity of the disease condition, the manner of administration and the like, which can readily be determined by one of ordinary skill in the art. The pharmaceutically acceptable salt of azelastine may be administered in either single or multiple doses by oral administration. Administration may be via capsule, tablet, or the like.

As used herein, the term "about" used in the context of quantitative measurements means the indicated amount ±10%. For example, with a ±10% range, "about 5 mg" can mean 4.5-5.5.

The oral dosage forms of azelastine or a pharmaceutically acceptable salt of azelastine in the amount of from about 4 mg to about 40 mg may be formulated for pharmaceutical use using methods known in the art, for example, Ansel's Pharmaceutical Dosage Forms and Drug Delivery Systems Tenth (by Loyd Allen, 2013) and Handbook of Pharmaceutical Manufacturing Formulations (Volumes 1-6 by Sarfaraz K. Niazi). Accordingly, incorporation of the active compounds and a controlled, or slow release matrix may be implemented.

Either fluid or solid unit dosage forms can be readily prepared for oral administration. For example, admixed with conventional ingredients such as dicalcium phosphate, magnesium aluminum silicate, magnesium stearate, calcium sulfate, starch, talc, lactose, acacia, methyl cellulose and functionally similar materials as pharmaceutical excipients or carriers. A sustained release formulation may optionally be used. In older or incoherent subjects, sustained release formulations may even be preferred. Capsules may be formulated by mixing the compound with a pharmaceutical diluent which is inert and inserting this mixture into a hard gelatin capsule having the appropriate size. If soft capsules are desired, a slurry of the pharmaceutically acceptable salt of azelastine with an acceptable vegetable, light petroleum or other inert oil can be encapsulated by forming into a gelatin capsule.

Suspensions, syrups and elixirs may be used for oral administration or fluid unit dosage forms. A fluid preparation including oil may be used for oil soluble forms. A vegetable oil such as corn oil, peanut oil or a flower oil, for example, together with flavoring agents, sweeteners and any preservatives produces an acceptable fluid preparation. A surfactant may be added to water to form a syrup for fluid unit dosages. Hydro-alcoholic pharmaceutical preparations may be used having an acceptable sweetener, such as sugar, saccharin or a biological sweetener and a flavoring agent in the form of an elixir.

The solid oral dosage formulation of the pharmaceutically acceptable salt of azelastine in this disclosure means a form of tablets, caplets, bi-layer tablets, film-coated tablets, pills, capsules, or the like. Tablets in accordance with this disclosure can be prepared by any mixing and tableting techniques that are well known in the pharmaceutical formulation industry. In some examples, the dosage formulation is fabricated by direct compressing the respectively prepared sustained-release portion and the immediate-release portion by punches and dies fitted to a rotary tableting press, ejection or compression molding or granulation followed by compression.

The pharmaceutically acceptable salt of azelastine provided in accordance with the present disclosure are usually administered orally. This disclosure therefore provides a pharmaceutically acceptable salt of azelastine that comprise a solid dispersion comprising a pharmaceutically acceptable salt of azelastine in the amount of from about 4 mg to about 40 mg as described herein and one or more pharmaceutically acceptable excipients or carriers including but not limited to, inert solid diluents and fillers, diluents, including sterile aqueous solution and various organic solvents, permeation enhancers, solubilizers, disintegrants, lubricants, binders, glidants, adjuvants, and combinations thereof. Such compositions are prepared in a manner well known in the pharmaceutical art (see, e.g., Ansel's Pharmaceutical Dosage Forms and Drug Delivery Systems, Tenth (by Loyd Allen, 2013) and Handbook of Pharmaceutical Manufacturing Formulations (Volumes 1-6 by Sarfaraz K. Niazi)).

The pharmaceutically acceptable salt of azelastine in the amount of from about 4 mg to about 40 mg may further comprise pharmaceutical excipients such as diluents, binders, fillers, glidants, disintegrants, lubricants, solubilizers, and combinations thereof. Some examples of suitable excipients are described herein. When the pharmaceutically acceptable salt of azelastine in the amount of from about 4 mg to about 40 mg is formulated into a tablet, the tablet may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

In certain embodiments, the pharmaceutically acceptable salts of azelastine are administered as daily effective amounts of from about 4 mg to about 40 mg of azelastine HCl or from about 4 mg to about 20 mg of azelastine HCl or from about 8 mg to about 16 mg of azelastine HCl It will be understood, that the amount of azelastine HCl actually administered usually will be determined by a physician, in the light of the relevant circumstances, including the condition to be treated, the chosen route of administration, the age, weight and response of the individual patient, the severity of the patient's symptoms, and the like.

The pharmaceutically acceptable salts of azelastine as described herein are administered to a patient suffering from mental, behavioral, cognitive disorders and other neurodegenerative disorders, such as Alzheimer's disease, with a daily effective amount of from about 4 mg to about 40 mg by oral administration once daily, twice daily, once every other day, once a week, two times a week, three times a week, four times a week, or five times a week.

In some embodiments, the pharmaceutical dosage forms, and tablets of the pharmaceutically acceptable salts of azelastine in a daily effective amount of from about 4 mg to about 40 mg as described in this specification are effective for reversing symptoms in patients suffering from early, middle or late stage Alzheimer's disease in about 6-24 weeks.

The following Examples are illustrative and should not be interpreted to limit the scope of the claimed subject matter. The Examples show that after 6 months of treatment with 12 mg azelastine HCl, both patients improved significantly on memory, language, reasoning, and time arrangement. Mini-Mental State Examination (MMSE) was not assessed but it is reasonable to predict that MMSE would have been significantly improved if measured.

Example 1

An 80 year old female patient with a weight of 51 kilograms and diagnosed with late-stage Alzheimer's disease for 6 years required round-the-clock assistance for her daily activities such as walking and looking for things, as well as personal care and her speech was limited to only a few words. She had very little awareness of her surroundings before being treated with 12 mg azelastine HCl once daily before bedtime. After 6 weeks of treatment with 12 mg azelastine HCl once daily before bedtime, she was able to walk in her house with light assistance. After 12 weeks of treatment, she was able to speak for more than 1 minute, know activities in her house and ask questions about daily activities in her house. After 6 months of treatment, she was a completely different person in terms of what she was able to do in comparison to what she could do before treatment, and she could actively talk to people and did not require assistance for her daily activities and personal care. Accordingly, her MMSE scores would similarly have been expected to have improved. Her weight gained by 3 kilograms after the 6 month treatment.

Example 2

An 83 year old female with a weight of 49 kilograms was diagnosed with mid- to late-stage Alzheimer's disease. Her daily activities were limited because she couldn't recall things which just occurred and could not locate anything that she wanted to retrieve by herself. She required assistance for most of her daily activities including personal care before she started the treatment of 12 mg azelastine HCl once daily before bedtime. After 6 weeks of treatment, she started to show signs that she was able to find a few things which she intended to retrieve. After 3 months of treatment, she required assistance for only a few daily activities or personal care and could do most of them by herself. Her MMSE scores would similarly have been expected to have improved. Her weight gained by 2.5 kilograms after the 6 month treatment.

REFERENCES

Sucher N J, Lipton S A, Dreyer E B. Molecular basis of glutamate toxicity in retinal ganglion cells. Vision Res. 1997; 37(24):3483-3493.

Koh J Y, Yang L L, Cotman C W. Beta-amyloid protein increases the vulnerability of cultured cortical neurons to excitotoxic damage. Brain Res. 1990; 533(2):315-320.

Harkany T, Abraham I, Timmerman W, et al. Beta-amyloid neurotoxicity is mediated by a glutamate-triggered excitotoxic cascade in rat nucleus basalis. Eur J Neurosci. 2000; 12(8):2735-2745.

Zeevalk G D, Nicklas W J. Evidence that the loss of the voltage-dependent Mg2+ block at the N-methyl-D-aspartate receptor underlies receptor activation during inhibition of neuronal metabolism. J Neurochem. 1992; 59(4): 1211-1220.

Lipton S A, Nicotera P. Calcium, free radicals and excitotoxins in neuronal apoptosis. Cell Calcium. 1998; 23:2-3. 165-171.

Gelosa P, Colazzo F, Tremoli E, Sironi L, Castiglioni L. Cysteinyl Leukotrienes as Potential Pharmacological Targets for Cerebral Diseases. Mediators Inflamm. 2017 May 10.

Alzheimer's Disease Internationl, "World Alzheimer Report 2010: the global economic impact of dementia."

R. S. Doody, J. K. Dunn, C. M. Clark et al., "Chronic donepezil treatment is associated with slowed cognitive decline in Alzheimer's disease," Dementia and Geriatric Cognitive Disorders, vol. 12, no. 4, pp. 295-300, 2001.

E. Schwam and Y. Xu, "Cognition and function in Alzheimer's disease: Identifying the transitions from moderate to severe disease," Dementia and Geriatric Cognitive Disorders, vol. 29, no. 4, pp. 309-316, 2010.

M. R. Farlow, M. L. Miller, and V. Pejovic, "Treatment options in Alzheimer's disease: maximizing benefit, managing expectations," Dementia and Geriatric Cognitive Disorders, vol. 25, no. 5, pp. 408-422, 2008.

A. Atri, L. W. Shaughnessy, J. J. Locascio, and J. H. Growdon, "Long-term course and effectiveness of combination therapy in Alzheimer disease," Alzheimer Disease and Associated Disorders, vol. 22, no. 3, pp. 209-221, 2008.

A. Atri, S. D. Rountree, 0. L. Lopez, and R. S. Doody, "Validity, significance, strengths, limitations, and evidentiary value of real-world clinical data for combination therapy in Alzheimer's disease: comparison of efficacy and effectiveness studies," Neurodegenerative Diseases, vol. 10, no. 1-4, pp. 170-174, 2012.

C. W. Zhu and M. Sano, "Economic considerations in the management of Alzheimer's disease," Clinical interventions in aging, vol. 1, no. 2, pp. 143-154, 2006.

Epstein A B, van Hoven P T, Kaufman A, Can W W. Management of allergic conjunctivitis: An evaluation of the perceived comfort and therapeutic efficacy of olopatadine 0.2% and azelastine 0.05% from two prospective studies. Clin Ophthalmol. 2009; 3:329-336.

Bielory L, Bielory B. Ocular allergy: An allergist's perspective. Aug. 16, 2010.

Pflugfelder S C. Prevalence, burden, and pharmacoeconomics of dry eye disease.

Am J Manag Care. 2008; 14 Suppl 3:S102-S106.

Bielory L, Lien K W, Bigelsen S. Efficacy and tolerability of newer antihistamines in the treatment of allergic conjunctivitis. Drugs. 2005; 65:215-218.

Bielory L, Buddiga P, Bigelsen S. Ocular allergy treatment comparisons: Azelastine and olopatadine. Curr Allergy Asthma Rep. 2004; 4:320-325.

Baudouin C. Detrimental effect of preservative in eye drops: Implications for the treatment of glaucoma. Acta Ophthalmologica. 2008; 86:716-726.

Lee J S, Lee J E, Kim N, Oum B S. Comparison of the conjunctival toxicity of topical ocular antiallergic agents. J Ocul Pharmacol Ther. 2008; 24:557-562.

Lambiase A, Micera A, Bonini S. Multiple action agents and the eye: Do they really stabilize mast cells? Curr Opin Allergy Clin Immunol. 2009; 9:454-465.

Casale T. The interaction of azelastine with human lung histamine H1, beta, and muscarinic receptor-binding sites. J Allergy Clin Immunol. 1989; 83:771-776.

Hazama H, Nakajima T, Hisada T, Hamada E, Omata M, Kurachi Y. Effects of azelastine on membrane currents in tracheal smooth muscle cells isolated from the guinea-pig. Eur J Pharmacol. 1994; 259: 143-150.

Perhach J L, Connell J T, Kemp J P. Treatment of upper and lower airway disease with azelastine. N Engl Reg Allergy Proc. 1987; 8:121-124.

Szelenyi I, Achterrath-Tuckermann U, Schmidt J, Minker E, Paegelow I, Werner H. Azelastine: A multifaceted drug for asthma therapy. Agents Actions Suppl. 1991; 34:295-311.

Galatowicz G, Ajayi Y, Stern M E, Calder V L. Ocular antiallergic compounds selectively inhibit human mast cell cytokines in vitro and conjunctival cell infiltration in vivo. Clin Exp Allergy. 2007; 37:1648-1656.

Ciprandi G, Pronzato C, Passalacqua G, et al. Topical azelastine reduces eosinophil activation and intercellular adhesion molecule-1 expression on nasal epithelial cells: An antiallergic activity. J Allergy Clin Immunol. 1996; 98(6 Pt 1):1088-1096.

Simons F E, Simons K J. Clinical pharmacology of new histamine H1 receptor antagonist. Clin Pharmacokinet. 1999; 36:329-352.

Loyd Allen, Ansel's Pharmaceutical Dosage Forms and Drug Delivery Systems, Tenth (2013). Sarfaraz K. Niazi, Handbook of Pharmaceutical Manufacturing Formulations Volumes 1-6.

The present invention has been described with reference to particular embodiments having various features. In light of the disclosure provided above, it will be apparent to those skilled in the art that various modifications and variations can be made in the practice of the present invention without departing from the scope or spirit of the invention. One skilled in the art will recognize that the disclosed features may be used singularly, in any combination, or omitted based on the requirements and specifications of a given application or design. When an embodiment refers to "comprising" certain features, it is to be understood that the embodiments can alternatively "consist of" or "consist essentially of" any one or more of the features. Any of the methods disclosed herein can be used with any of the compositions disclosed herein or with any other compositions. Likewise, any of the disclosed compositions can be used with any of the methods disclosed herein or with any other methods. Other embodiments of the invention will be apparent to those skilled in the art from consideration of the specification and practice of the invention.

It is noted in particular that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the invention fall within the scope of the invention. Further, all of the references cited in this disclosure are each individually incorporated by reference herein in their entireties and as such are intended to provide an efficient way of supplementing the enabling disclosure of this invention as well as provide background detailing the level of ordinary skill in the art.

The invention claimed is:

1. A method comprising orally administering an oral formulation to a patient having Alzheimer's disease, daily and for a period of at least six weeks, the oral formulation comprising about 12 mg to about 40 mg azelastine or a pharmaceutically acceptable salt of azelastine, thereby improving the patient's quality of life as demonstrated by the patient requiring less need for support with the patient's activities of daily living.

2. The method of claim 1, wherein the pharmaceutically acceptable salt of azelastine is azelastine hydrochloride.

3. The method of claim 1, wherein the oral formulation comprises about 12 mg to about 20 mg of the azelastine or the pharmaceutically acceptable salt of azelastine.

4. The method of claim 2, wherein the oral formulation is a solid form or a liquid form.

5. The method of claim 1, wherein the oral formulation comprises 16 mg to 20 mg azelastine or a pharmaceutically acceptable salt of azelastine.

6. A method comprising orally administering an oral formulation to a patient having Alzheimer's disease, the oral formulation comprising about 12 mg to 40 mg azelastine or a pharmaceutically acceptable salt of azelastine, whereby the oral formulation is administered daily and for a period of time to improve one or more symptoms of the patient's Alzheimer's disease as measured by Mini-Mental State Examination (MMSE).

7. The method of claim 6, wherein the oral formulation is administered for a period of time to improve one or more symptoms of the patient's Alzheimer's disease as measured by Neuropsychiatric Inventory (NPI) and Activities of Daily Living (ADL).

8. The method of claim 6, wherein the oral formulation comprises about 12 mg to about 20 mg of the azelastine or the pharmaceutically acceptable salt of azelastine.

9. The method of claim 7, wherein the oral formulation comprises about 12 mg to about 20 mg of the azelastine or the pharmaceutically acceptable salt of azelastine.

* * * * *